United States Patent [19]

Parish et al.

[11] Patent Number: 5,976,782
[45] Date of Patent: *Nov. 2, 1999

[54] IN-VITRO ANGIOGENESIS ASSAY

[75] Inventors: Christopher Richard Parish, Campbell; Kathryn Joanna Isabel Brown, Dickson; Susan Faye Maynes, Ngunnawal; Anna Bezos, Reid, all of Australia

[73] Assignee: The Australian University, Australia

[*] Notice: This patent issued on a continued prosecution application filed under 37 CFR 1.53(d), and is subject to the twenty year patent term provisions of 35 U.S.C. 154(a)(2).

[21] Appl. No.: 08/702,578
[22] PCT Filed: Mar. 3, 1995
[86] PCT No.: PCT/AU95/00105
§ 371 Date: Oct. 31, 1996
§ 102(e) Date: Oct. 31, 1996
[87] PCT Pub. No.: WO95/23968
PCT Pub. Date: Sep. 8, 1995

[30]    Foreign Application Priority Data

Mar. 4, 1994  [AU]  Australia ............... PM4252/94

[51] Int. Cl.$^6$ ...................................... C12N 5/00
[52] U.S. Cl. .................................. 435/4; 435/29; 435/325
[58] Field of Search .................................. 435/4, 29, 325

[56]            References Cited

PUBLICATIONS

Nicosia, R.F. et al. "Large–vessel endothelium switches to a microvascular phenotype during angiogenesis in collagen gel culture of rat aorta" Atherosclerosis, 95, 1992, pp. 191–199.

Nicosia, R.F. et al. "Growth of Microvessels in Serum–Free Matrix Culture of Rat Aorta"; Laboratory Investigation, 63, (1) 1990, pp. 115–122.

Gajdusek, C.M. et al. "Basic Fibroblast Growth Factor and Transforming Growth Factor Beta–1" Journal of cellular physiology, 157, 1993, pp. 133–144.

*Primary Examiner*—Leon B. Lankford, Jr.
*Attorney, Agent, or Firm*—Fulwider Patton Lee & Utecht

[57]                ABSTRACT

The present invention relates to methods for determining angiogenesis comprising culturing a blood vessel fragment in a physiological gel. In addition the invention provides a method for testing substances for their ability to modulate angiogenesis and a method of determining whether an angiogenic entity such as a tumour will be responsive to anti-angiogenic therapy.

45 Claims, 5 Drawing Sheets

IN-VITRO ANGIOGENESIS ASSAY

The present invention relates to a method for determining angiogenesis, a method of screening substances for angiogenesis modulation activity, and a method of determining the appropriate treatment regime in the case of tumours and the like.

BACKGROUND OF THE INVENTION

Angiogenesis, or the development of new blood vessels, is an essential feature of tissue development and wound healing (1). Without the appropriate development of a blood supply, tissues cannot survive; the circulatory system being essential for the supply of oxygen and nutrients to tissues and for removal of by products of metabolism.

In adults, angiogenesis is a relatively rare occurrence except during wound healing. However, there are a number of "angiogenesis-dependent diseases" in adults where angiogenesis is of critical importance (1–3). The most important of these is the angiogenesis associated with the growth of solid tumours, proliferative retinopathies and rheumatoid arthritis. The development of angiogenesis inhibitors may provide a means for controlling these diseases but current assays for angiogenesis are cumbersome, time consuming and usually based on in vivo systems. The three most frequently used models are the rabbit corneal pocket, the hamster cheek pouch and the chicken chorioallantoic membrane (CAM) assays (1–4). In each system an angiogenic substances must be implanted in the cornea, cheek pouch or the CAM in order to induce angiogenesis. All three assays suffer from the need to artificially induce angiogenesis, the requirement for a sustained-release polymeric vehicle for the angiogenic substance and inhibitor (5), and the technical complexities associated with setting up the assay, including using live animals, and measuring the outcome. The rabbit corneal assay has the additional disadvantage of being ethically unacceptable in many research institutions.

Because of these disadvantages there is a great need for physiologically relevant, in vitro assays for angiogenesis, particularly human angiogenesis. Previous in vitro assays have usually entailed establishing long term cultures of endothelial cells and inducing formation of microvessels by placing the cells on extracellular matrices (6–8) or exposing the cells to various angiogenic stimuli (9–11). Such assays are highly artificial and may not represent a physiological response, particularly as the endothelial cells are already activated, having been cultured for considerable periods of time in the presence of growth factors before use.

The in vitro assay of the present invention represents an angiogenic response which mirrors a normal physiological response, namely neo-vascularisation following blood vessel damage. In one embodiment, the assay of the present invention provides substantial advantages over a previously described procedure where a large volume of frequently replaced culture medium is necessary (12). This is because, in one embodiment, use of a miniaturised assay makes it feasible to test pro- and antiangiogenic substances. Furthermore, the overall cost of the assay (i.e. labour costs, media and tissue flask expenses) is dramatically reduced and the assay, when conducted in a convenient 24 or 48 well format, allows rapid examination and quantification by light microscopy. In addition the assay in all of its embodiments is ethically acceptable because it avoids the use of live animals. Furthermore it provides direct information about the effects of particular angiogenic modulating substances on a particular species because vascular tissue from that species can be used in the assay. For example the assay can directly determine whether a particular substance has angiogenic modulating ability in humans since human tissue may be used in the assay.

In work leading up to the present invention, the inventors discovered that small fragments of human placental blood vessels embedded in a fibrin clot displayed a complex network of blood vessels growing out of the vessel fragment following 7–14 days culture. The assay was performed in 24 or 48 well culture plates with the use of small volumes of media (0.5–1 ml/well) with infrequent media changes (twice weekly). It is expected that physiological gels other than fibrin will produce a similar response.

The angiogenic response found by the present inventors appears to be totally spontaneous, not requiring the addition of angiogenic factors to the cultures, and without wishing to be bound by theory, presumably represents the wound healing response of a severed blood vessel.

SUMMARY OF THE INVENTION

In a first aspect the invention provides a method for obtaining angiogenesis comprising culturing a blood vessel fragment together with a physiological gel and suitable nutrients for a time sufficient to allow growth of new vascular tissue, wherein the fragment is cultured on a miniaturised scale and wherein said nutrients are replaced infrequently.

In a related aspect the invention provides a method for determining angiogenesis comprising culturing a blood vessel fragment together with a physiological gel and suitable nutrients for a time sufficient to allow growth of new vascular tissue, and examining said fragment to determine whether new vascular tissue has grown, wherein the fragment is cultured on a miniaturised scale and wherein said nutrients are replaced infrequently.

In another aspect the present invention provides a method for determining angiogenesis comprising culturing a blood vessel fragment from a sample of human tissue together with a physiological gel and suitable nutrients for a time sufficient to allow growth of new vascular tissue, and examining said fragment to determine whether new vascular tissue has grown.

In another aspect the invention provides a method for testing substances for angiogenesis modulation activity comprising culturing a blood vessel fragment from a biological sample together with a physiological gel, suitable nutrients and at least one substance suspected of having angiogenesis modulation activity for a time and under conditions sufficient to allow growth of new vascular tissue, examining said fragment for new vascular tissue growth and comparing said growth to that of a control.

In yet another aspect the invention provides a method for determining the ability of a substance to prevent growth of new vascular tissue and/or induce regression of new vascular tissue comprising culturing a blood vessel fragment together with a physiological gel and suitable nutrients for a time sufficient to allow growth of new vascular tissue, administering the substance to said fragment, and culturing said fragment together with suitable nutrients for a time, then examining said fragment to determine whether prevention of new vascular tissue growth and/or regression of new vascular tissue has occurred.

In still another aspect the invention provides a method of determining whether an angiogenic entity will be responsive to anti-angiogenic therapy said method comprising culturing blood vessel fragments from said entity together with a physiological gel, suitable nutrients and an effective amount of at least one anti-angiogenic agent for a time and under conditions sufficient to allow growth of new vascular tissue, examining said fragments for new vascular tissue growth and comparing said growth to that of a control.

In another aspect the invention provides a kit comprising in compartmentalized form a first compartment or compartments adapted to receive a physiological gel for culturing of a blood vessel fragment, wherein said first compartment or compartments is optionally adapted to contain one or more physiological gel precursors, a second compartment or compartments adapted to contain nutrients or a nutrient medium for addition to the physiological gel to support growth of a blood vessel fragment, and optionally frozen blood vessel fragments.

DETAILED DESCRIPTION OF THE INVENTION

Figure 1A:
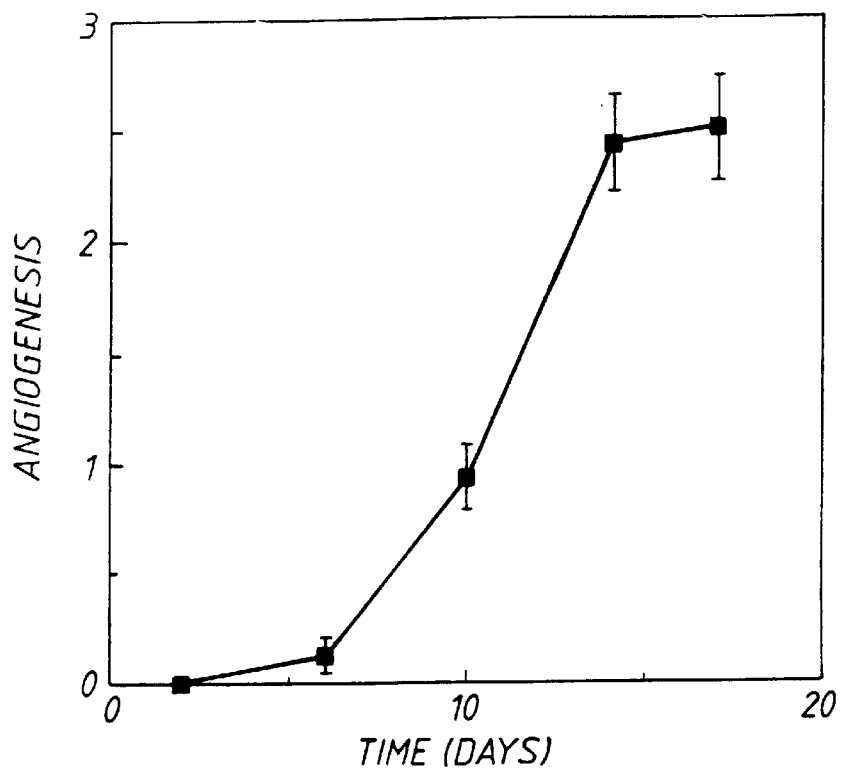

In one aspect the present invention provides a method for obtaining angiogenesis comprising culturing a blood vessel fragment together with a physiological gel and suitable nutrients for a time sufficient to allow growth of new vascular tissue, wherein the fragment is cultured on a miniaturised scale and wherein said nutrients are replaced infrequently.

In a related aspect, the present invention provides a method for determining angiogenesis comprising culturing a blood vessel fragment together with a physiological gel and suitable nutrients for a time sufficient to allow growth of new vascular tissue, and examining said fragment to determine whether new vascular tissue has grown, wherein the fragment is cultured on a miniaturised scale and wherein said nutrients are replaced infrequently.

The term "physiological gel" used herein means a gel which mimics, or partially mimics the physiological environment within an organism which allow angiogenesis to occur. Preferably the physiological gel is fibrin, collagen or matrigel or similar. Most preferably the gel is fibrin.

The term "miniaturised scale" used herein means the use of small volumes of media. Suitable culture vessels for the miniaturised scale include microplates where liquid volumes of about 0.5–1 ml or less can be used as opposed to larger systems where typically tens of millilitres are used. Preferably volumes of 0.5–1 ml or less are used in the cultures of the present invention. Preferably exogenous factors which provide angiogenic stimuli are not added to the medium.

The term "infrequently" used herein in relation to nutrient replacement refers to a nutrient replacement occurring less frequently than every second day. Preferably nutrient replacement is twice a week, more preferably once every four days, in the method of the present invention.

Blood vessel fragments used in the methods may be derived from either venular or arterial origin and are preferably of a small size. For example, blood vessels with an approximate diameter of 1 to 2 mm and 2 to 5 cm in length are suitable for the production of fragments which are preferably 1 to 2 mm in length. Preferably the blood vessel fragments are freshly isolated. Alternatively frozen blood vessel fragments may be used.

Preferably the blood vessels fragment used in the method is derived from human tissue, for example, human tissue which is readily available such as placentas and solid tumours. It will, of course, be appreciated that the method of the invention could also be used to assay angiogenesis in non-human blood vessel fragments.

Preferably the blood vessels fragment used in the methods is freed from residual blood clots prior to culturing. This may be done by soaking the blood vessel fragment in any buffer suitable for the purpose. Such buffers will be known by those skilled in the art.

Preferably the physiological gel used in the methods is freshly prepared. Even more preferably the blood vessel fragment is added to the physiological gel precursors prior to clot formation. Still more preferably the blood vessel fragment is embedded in and surrounded by the gel.

The nutrients are preferably supplied in a liquid medium such as Medium 199 optionally containing 20% foetal calf serum and may also contain, in addition, antibiotics to inhibit the growth of microorganisms. Alternatively the medium may be a substantially serum free medium. The term "substantially serum free " used herein means that whole serum is absent and the medium has no serum constituents or a minimal number of constituents from serum or other sources which are necessary for angiogenesis. Those skilled in the art will be familiar with the appropriate media.

In the method the blood vessel fragment is cultured under suitable conditions to allow the growth of new vascular tissue. Those skilled in the art will be familiar with the various suitable conditions which may be used to culture the fragments. Preferably the blood vessel fragment is grown at about 37° C. for about two to three weeks.

Examination of the blood vessel fragment may be carried out by any convenient means. Preferably examination of the blood vessel fragments is carried out by bright field or phase contrast light microscopy. This may be done using an inverted microscope.

The responses of the fragments (angiogenic or otherwise) can be quantified manually or by computer based image analysis of photographs, video images or digital images of the cultures. Preferably the responses are quantified by automated means such as by the NIH IMAGE program. Such quantification provides rapid and accurate assessment of the responses. In addition, such an assay system is particularly well suited to screening inhibitors or enhancers of human angiogenesis. Those skilled in the art will be familiar with the various ways of quantifying the responses of the fragments.

In a second aspect, the present invention provides a method for determining angiogenesis comprising culturing a blood vessel fragment from a sample of human tissue together with a physiological gel and suitable nutrients for a time sufficient to allow growth of new vascular tissue, and examining said fragment to determine whether new vascular tissue has grown.

Preferably the tissue used in the method is placental tissue, or another tissue from which blood vessels may be isolated.

Preferably blood vessel fragments are cultured in small culture vessel including culture plates. Preferably the medium is changed infrequently, such as twice weekly. Preferably the physiological gel is fibrin, collagen or matrigel. More preferably the gel is fibrin.

In the prior art it has been necessary to add agents which enhance angiogenesis to the culture medium. In the method of the present invention, however, it has been found that such agents are not necessary. Thus in a preferred aspect, additional angiogenic agents are not added to the culture medium.

In a third aspect the present invention provides a method for screening substances for angiogenesis modulation activity comprising culturing a blood vessel fragment from a biological sample together with a physiological gel, suitable nutrients and at least one substance suspected of having angiogenesis modulation activity for a time and under conditions sufficient to allow growth of new vascular tissue, examining said fragment for new vascular tissue growth and comparing said growth to that of a control.

The term "screening" refers to testing or assaying the substance.

The term "angiogenesis modulation" refers to the ability of a substance to modulate or change normal angiogenic activity of the blood vessel fragments and includes inhibition and enhancement of angiogenic activity. The method may be used to test compounds or substances which are possible angiogenesis inhibitors or possible angiogenesis enhancers.

The term "biological sample" refers to any sample which is ultimately derived from an animal tissue where it is desirable to test whether a substance has angiogenesis modulation activity for that particular tissue and/or animal species. Preferably the biological sample is derived from human tissue.

Any substance, or combination of substances which are suspected of angiogenesis modulation activity may be screened by the method. This includes purified preparations of compounds and various extracts such as plant or animal tissue extracts or may be from a microorganism. Accordingly, such substances may have to be brought into a suitable form for administration to the blood vessel fragments. Those skilled in the art will be familiar with various methods for bringing such substances into suitable form for administration.

As mentioned above, blood vessel fragments may be derived from venular or arterial origin. Preferably the fragments from the one blood vessel are used both for the control and cultures being screened with potential angiogenesis modulation activity.

Preferably the physiological gel is fibrin, collagen or matrigel. More preferably the gel is fibrin.

Preferably when the method is used to test compounds for angiogenesis enhancement the medium is substantially serum free (as previously defined).

In a related aspect, the present invention provides a method for determining the ability of a substance to prevent growth of new vascular tissue and/or induce regression of new vascular tissue comprising culturing a blood vessel fragment together with a physiological gel and suitable nutrients for a time sufficient to allow growth of new vascular tissue, administering the substance to said fragment, and culturing said fragment together with suitable nutrients for a time, then examining said fragment to determine whether prevention of new vascular tissue growth and/or regression of new vascular tissue has occurred.

Preferably, the blood vessel fragment is cultured for a time sufficient to establish a good angiogenic response prior to the substance being administered, such as, for example, 14 days prior to administration. The extent of this response is then preferably quantified and recorded.

Preferably, after the substance is administered, the blood vessel fragment is cultured for a time sufficient to allow clear prevention and/or regression of new blood vessel growth, such as, for example, 7 to 14 days after the substance is administered. The state of the new blood vessel growth is then compared to the recorded response and preferably a control.

Preferably the physiological gel is fibrin, collagen or matrigel or the like. More preferably the gel is fibrin.

In a fourth aspect the present invention provides a method for determining whether an angiogenic entity will be responsive to anti-angiogenic therapy said method comprising culturing blood vessel fragments from said entity together with a physiological gel, suitable nutrients and an effective amount of at least one anti-angiogenic agent for a time and under conditions sufficient to allow growth of new vascular tissue, examining said fragments for new vascular tissue growth and comparing said growth to that of a control.

The term "angiogenic entity" includes tumours (particularly metastatic and invasive tumours) and test tissue from patients with other angiogenesis-dependent diseases such as rheumatoid arthritis and proliferative retinopathies.

The term "anti-angiogenic agent" means any compound or substance which inhibits angiogenesis. This may be a proteinaceous or non-proteinaceous molecule and includes corticosteroids, anti-growth factor antibodies and anti-angiogenic proteins such as platelet factor 4.

Preferably the physiological gel is fibrin collagen or matrigel.

The culture conditions utilised in the second, third and fourth aspects of the invention are preferably carried out under the same conditions which are preferred for the first embodiment of the invention as described above.

In a fifth aspect the present invention provides a kit comprising, in compartmentalized form a first compartment or compartments adapted to receive a physiological gel for culturing of a blood vessel fragment, wherein said first compartment or compartments is optionally adapted to contain one or more physiological gel precursors, a second compartment or compartments adapted to contain a nutrients or a nutrient medium to support growth of a blood vessel fragment and optionally frozen blood vessels.

The term "compartment" means a particular partition of a container or a separate container.

Preferably the kit provides a first compartment or compartments on a miniaturised scale such that only small volumes of medium may be used. Preferably the compartment or compartments is adapted to receive 0.5 to 1 mL of medium and is in the form of a multiwell tray such as a microwell plate such as, but not limited to, a 24 or 48 well plate.

Preferably the kit additionally comprises a further compartment or compartments which are adapted to contain a major physiological gel precursor such as fibrinogen or a collagen or matrigel precursor. This may be in freeze dried form or in suspension.

Preferably there is a third compartment or compartments which are adapted to contain the other relevant physiological gel precursor such as thrombin which may be in freeze dried form or in suspension.

Preferably the second compartment is adapted to contain a suitable medium such as medium 199 (or its constituents) or a substantially serum free medium (where substances are screened for angiogenesis enhancement activity).

Frozen blood vessels, particularly blood vessel fragments, may form part of the kit. The blood vessels may be of venular or arterial origin and are preferably 1 to 2 mm in diameter. Preferably the blood vessels are provided in the form of fragments, preferably of 1 to 2 mm in length. More preferably the blood vessels are of human origin, still more preferably of human placental origin.

The blood vessels may be frozen by standard techniques such as those known to the skilled artisan such as in culture medium containing DMSO at −70° C.

The kit described above is for use in the methods of the invention described earlier. The invention also extends to the kits when used in the above method.

The present invention is further described with reference to the following non-limiting Figures and Examples. In the Figures:

FIG. 1 is a graphic representation of in vitro angiogenesis of human placental vessel fragments embedded in a fibrin gel. In (A) the angiogenic response was scored manually on an arbitrary scale of 0 to 3 as outlined in the Materials and Methods. Each time point the mean±standard error of 8 cultures. In (B) the angiogenic response was quantified by computer based image analysis of digital images.

Figure 2A:
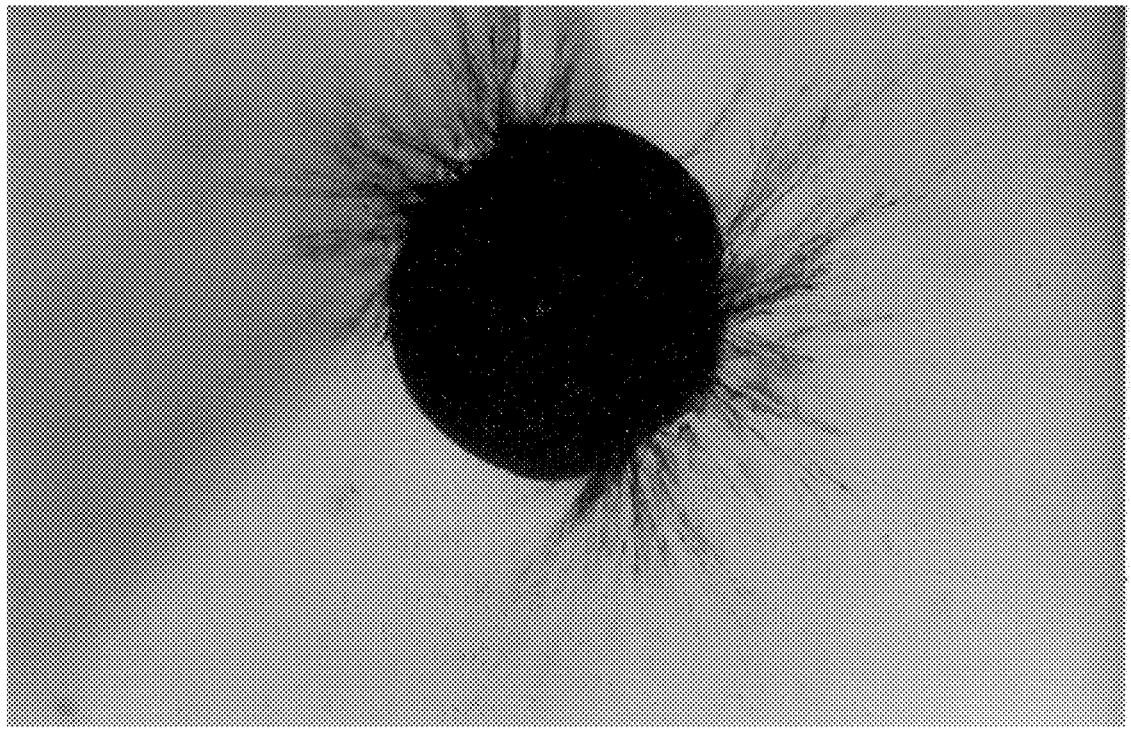
Figure 2B:
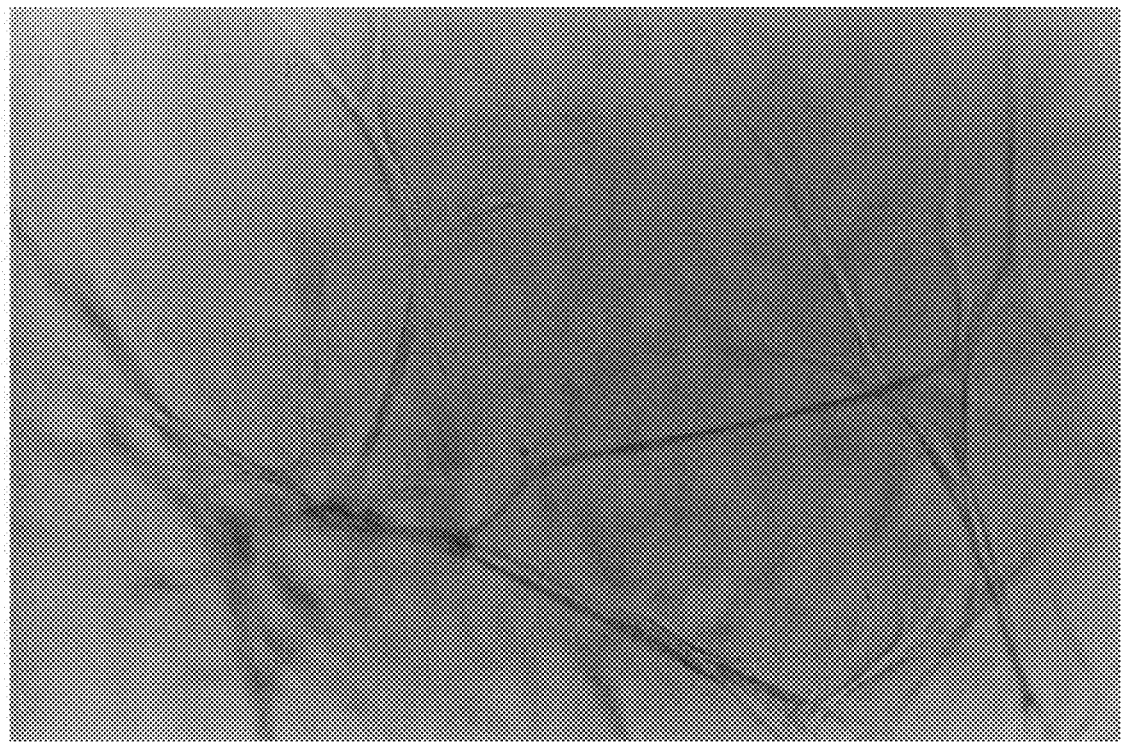

FIG. 2 shows photomicrographs of in vitro angiogenesis using fragments of human placental blood vessels embedded in a fibrin gel. Angiogenesis depicted after 14 days culture at (A)×25 and (B)×200 magnification. The angiogenic response in FIG. 2A was manually scored as 3.

Figure 3:
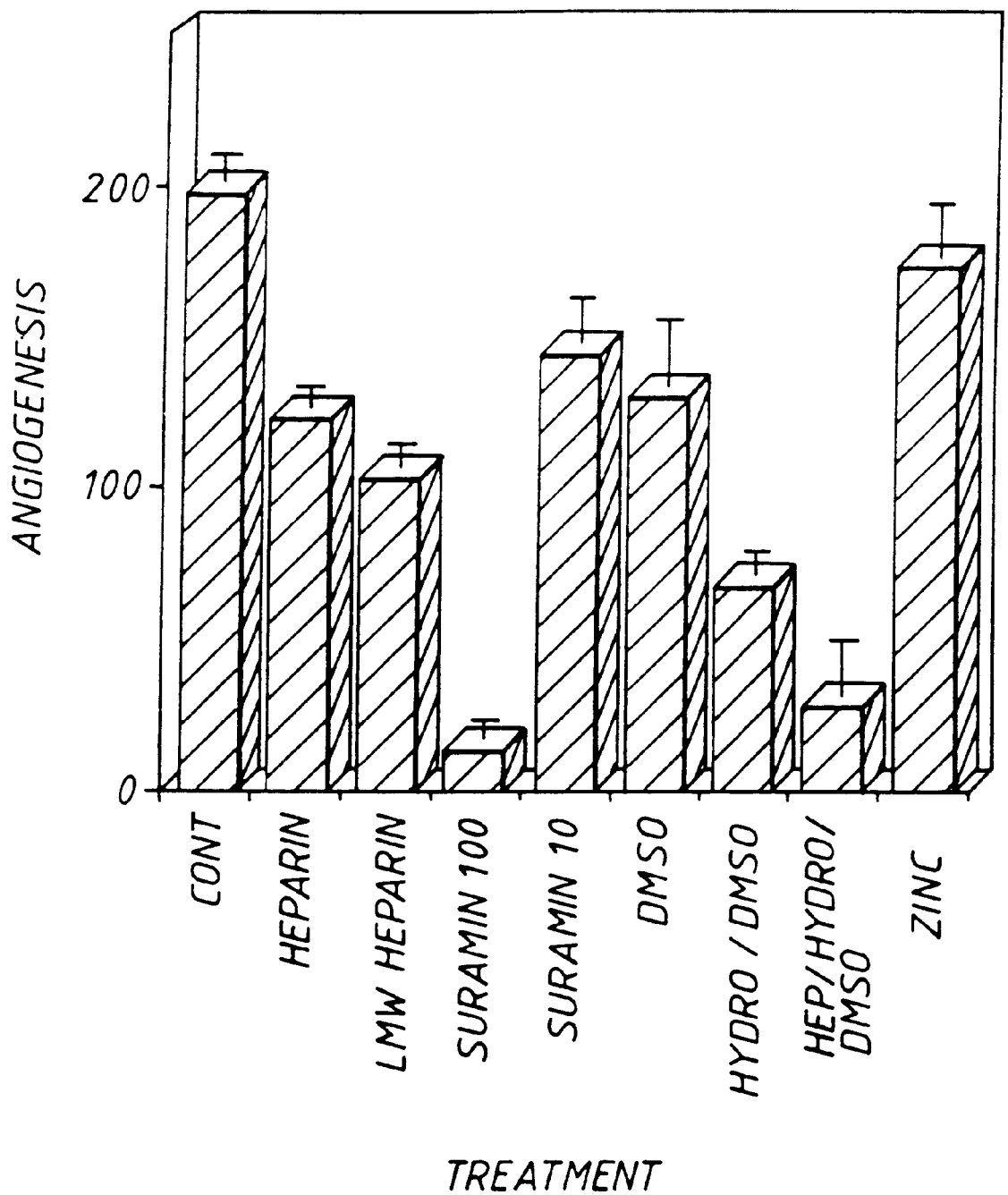

FIG. 3 is a graphic representation and demonstrates that the assay may be used to test the ability of different compounds to inhibit angiogenesis. Compounds were used at the following concentrations throughout the assay: heparin and low mol. wt. (LMW) heparin—100 µg/ml. suramin—10 µg/ml and 100 µg/ml as indicated, DMSO—0.5%, hydrocortisone (Hydro)—$10^{-5}$M and zinc—20 µM. "Cont" refers to a control culture where no compound was added. Data represents angiogenesis, as measured by digital image analysis, after 14 days of culture. Vertical bars represent standard errors of means (n=4).

Figure 4:
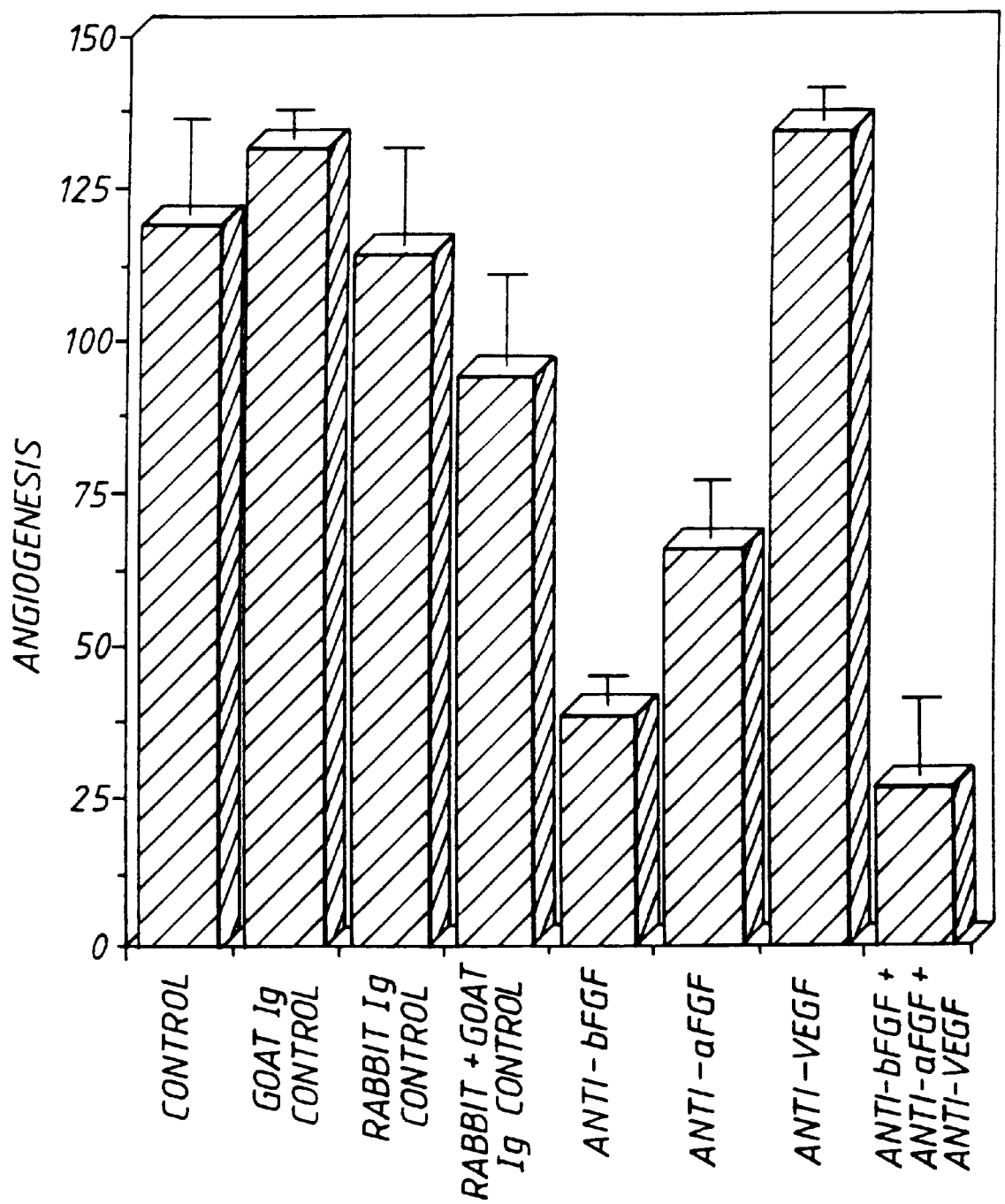

FIG. 4 is a graphic representation and demonstrates that the assay may be used to test the ability of polyclonal antibodies against the angiogenic growth factors aFGF, bFGF and VEGF to inhibit angiogenesis. The data is expressed as in FIG. 3. Control antibodies were used in the assay as indicated by goat Ig and rabbit Ig in the histogram annotations.

Figure 5:
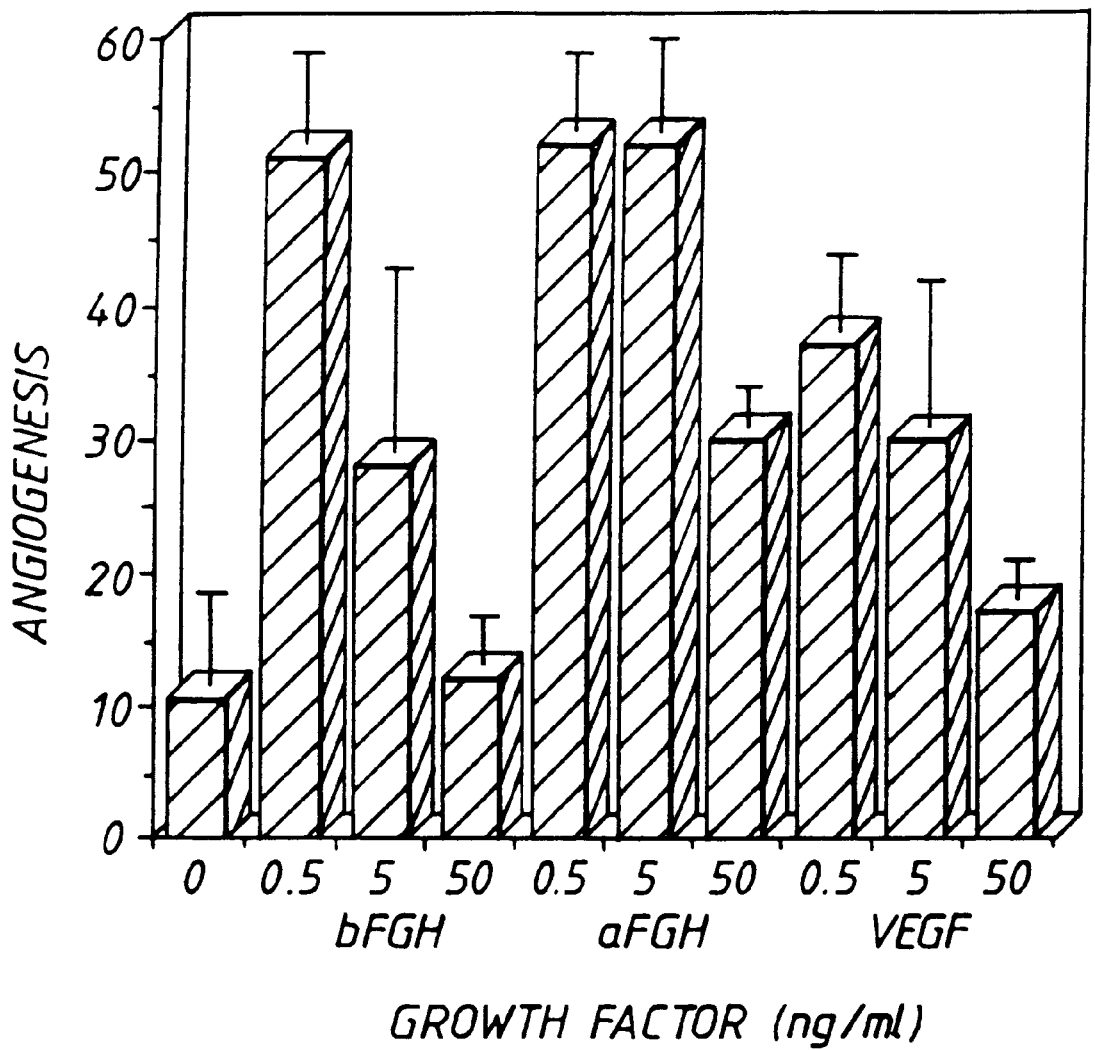

FIG. 5 is a graphic representation and demonstrates that the assay may also test the ability of different concentrations of bFGF, aFGF and VEGF to enhance human angiogenesis in serum starved cultures. The data is expressed as in FIG. 3. Note that at 50 ng/ml VEGF induced considerable "dieback" of vessels.

EXAMPLE 1

Angiogenesis Assay

A. Materials and Methods

Preparation of Blood Vessel Fragments

Blood vessels, approx 1–2 mm in diameter and 2–5 cm in length, were excised from the surface of human placentas within 6 hours of birth. The vessels were placed in Hank's BSS containing 2.5 µg/ml of fungizone and cut into 1–2 mm length fragments using fine dissecting forceps and iridectomy scissors. Vessel fragments were freed of residual clots and soaked in Hank's BSS before use. Dissecting and sectioning of vessels was performed with the aid of a magnifier lamp (Maggylamp, Newbound, Balmain. NSWA. Australia). Similar angiogenic responses were obtained from blood vessels of venular and arterial origin but for each assay, vessel fragments from only one vessel were used.

Angiogenesis Assay

Assays were performed in 24 or 48 well culture plates (Costar, Cambridge, Mass.). In the 24 well format 30 µl of bovine thrombin (50 NIH units/ml in 0.15 M NaCl; Sigma Chemical Co., St. Louis, Mo.) was added to each well followed by 1.0 ml/well of 3 mg/ml bovine fibrinogen (Sigma) in Medium 199. The thrombin and fibrinogen were mixed rapidly and one vessel fragment quickly placed in the centre of the well before clot formation. Usually fibrin gel formation occurred in 30 seconds and ideally the vessel fragment should remain suspended in the gel. Following gel formation 1.0 ml/well of Medium 199 supplemented with 20% foetal calf serum (FCS), 0.2 ml ε-aminocaproic acid, L-glutamine and antibiotics (gentamycin and fungazone) was added. In the 48 well format all reagent volumes were halved. Vessels were cultured at 37° C. in a humidified environment for 14–21 days with the medium being changed twice weekly. Angiogenesis was quantified, initially manually, using an arbitrary scale from 0–3 where 0=no growth, 1=sparse, 2=medium and 3=dense microvessel growth. More accurate assessment of angiogenesis was achieved by computer based image analysis, using NIH Image software, of digital images of the cultures obtained with a Dycam digital camera.

Immunohistochemistry

Fibrin gels containing angiogenic responses (i.e. new vascular growth) were fixed overnight in 4% paraformaldehyde in PBS at 4° C. in preparation for immunohistochemistry. The fixed gels were paraffin embedded and 3µ histological sections cut and mounted on poly-L-lysine coated microscope slides. Sections were microwave treated for 3 minutes and partially digested with 0.1% trypsin in 0.1% $CaCl_2$ in order to expose antigens. Sections were then reacted with antibodies and horse radish peroxidase coupled sheep $F(ab^1)_2$ anti-mouse Ig (Amersham, Amersham, Herts, U.K.) used as the detection system. The sections were reacted with diaminobenzidine with silver enhancement and counterstained with haematoxylin. Antibodies used were monoclonal mouse anti-human factor VIII related antigen (Dako. Denmark). an anti-human endothelial cell mAb (Gibco, Grand Island, N.Y.) and a CD31—specific mAb (clone 20G5) produced in the John Curtin School of Medical Research.

B. Results

Figure 1B:
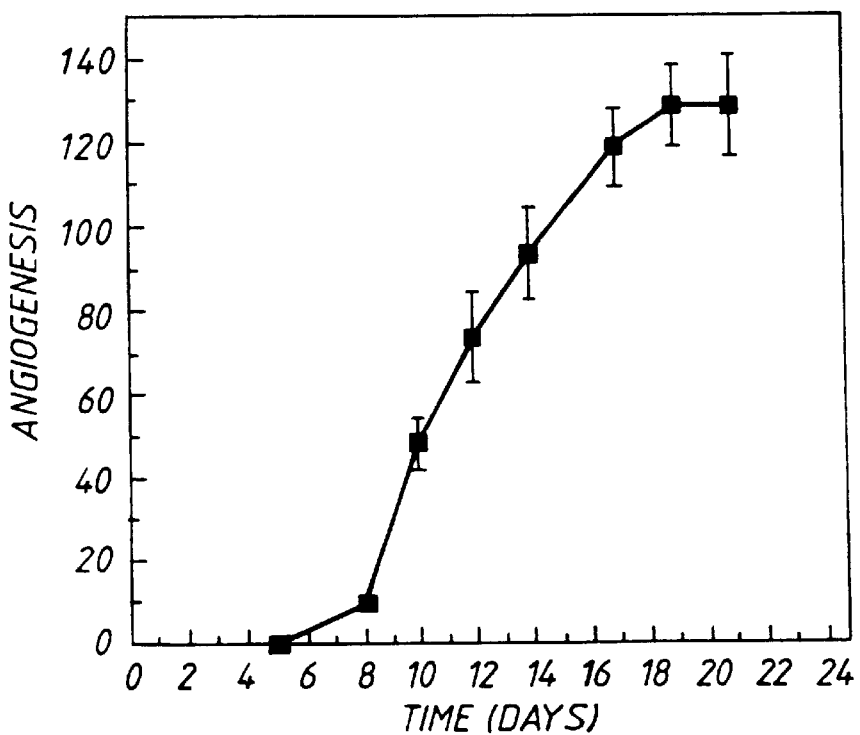

The results of a typical human angiogenesis assay are depicted in FIG. 1. Weak angiogenesis was detected after 6–8 days of culture and the angiogenic response plateaued at days 14–20. In FIG. 1A the assay was quantified by a manual scoring method and by a less subjective, computer based image analysis method in FIG. 1B.

Fibroblasts occasionally contaminated cultures but usually only appeared as a monolayer on the bottom of the culture wells as, unlike endothelial cells, fibroblasts cannot invade fibrin gels (13). Fibroblast outgrowth was negligible if vessel fragments were suspended in the fibrin gel rather than in contact with the plastic base of the culture wells. In order to inhibit clot retraction and resultant fibroblast contamination the fibrinolytic inhibitor, ε-aminocaproic acid, was included in the culture medium.

Comparable angiogenic responses were obtained with both arterial and venular vessels from human placenta. In fact, excised vessel could be stored overnight at 4° C. in Hank's BSS and still mounted a good angiogenic response when embedded in a fibrin gel. However, the response tended to be delayed 1–2 days compared with freshly isolated vessels. Angiogenesis occurred in the absence of exogenous growth factors and, in fact, addition of endothelial cell growth supplement+heparin had no detectable effect on angiogenesis. A weak angiogenic response was also sometimes observed in serum free medium although the responses were quite variable. Use of low serum medium (see Example 3) allowed the detection of factors which could enhance angiogenesis.

A typical 14 day angiogenic response is depicted in FIG. 2A. A dense and complex network of blood vessels penetrate considerable distances into the fibrin gel. At high magnification (FIG. 2B) branching of blood vessels can be clearly discerned.

Immunohistochemical staining of angiogenic samples revealed that all vessels were positive for Factor VIII related antigen, a reaction clearly demonstrating that the outgrowths are blood vessels. The vessels also reacted with a mAb specific for human endothelial cells (Gibco) and with a mAb to CD31, an antigen only expressed on endothelial cells, platelets and some leukocytes. Examination of angiogenic samples under the electron microscope also revealed cells with a classic endothelial morphology.

EXAMPLE 2

Screening of Substances for Angiogenic Inhibition

A. Materials and Methods similar to Example 1 except that separate aliquots of substances suspected of angiogenic inhibitor activity are added to individual wells. The substance to be tested for angiogenesis modulating activity is dissolved in an appropriate solution (e.g. water, DMSO) and diluted in Medium 199 containing 20% foetal calf serum. Immediately following the embedding of vessel fragments in the fibrin gels, 0.5–1.0 ml of medium containing the test substance is added to each well. Fresh medium containing test substances is added every 4 days. A group of control cultures receives medium with the appropriate dissolving solution but without a test substance added.

Following culture for 14–21 days, as in Example 1, angiogenesis is quantified and compared with control cultures. In the case of anti-angiogenic substances, a reduced growth of blood vessels compared with the control cultures will be observed.

Also, in some cases substances can be tested for their ability to induce regression of recently formed blood vessels by adding the test substance to established angiogenesis responses (i.e. after 14 days culture) and monitoring "dieback" of blood vessels microscopically for the next 7–14 days.

The following substances were tested:

heparin (100 $\mu$g/ml)

low molecular weight heparin (100 $\mu$g/ml)

suramin (100 $\mu$g/ml & 10 $\mu$g/ml)

3-hydrocortisone ($10^{-5}$M)

3-hydrocortisone ($10^{-5}$M) and heparin (100 $\mu$g/ml)

polyclonal neutralizing antibodies for acidic fibroblast growth factor (aFGF)

polyclonal neutralizing antibodies for basic fibroblast growth factor (bFGF)

mixture of polyclonal neutralizing antibodies for aFGF and bFGF polyclonal neutralizing antibodies for vascular endothelial growth factor (VEGF).

B. Results

This Example demonstrates that the present invention is effective in assaying known angiogenesis inhibitors.

FIG. 3 depicts the ability of a number of substances, which may possess antiangiogenic activity, to inhibit the in vitro angiogenesis response. Heparin and low mol. wt. heparin (100 $\mu$g/ml), which alone usually do not inhibit angiogenesis (1), exhibited a small but significant inhibition of angiogenesis in the assay shown. However, this inhibitory effect was not reproduced in other assays. In contrast, suramin at 100 $\mu$g/ml virtually totally inhibited angiogenesis whereas at 10 $\mu$g/ml the inhibitory activity of this compound was lost. These data are consistent with other studies which have shown that suramin possesses anti-angiogenic activity in vitro (14). Hydrocortisone alone, like heparin, usually has little or no anti-angiogenic activity (1). In the experiment depicted in FIG. 3 hydrocortisone, at the relatively high concentration of $10^{-5}$M, partially inhibited angiogenesis compared with the DMSO (0.5%) diluent control. However, a combination of heparin and hydrocortisone almost completely inhibited the angiogenic response. Such a result has been shown in vivo where heparin synergizes with steroids to cause regression of growing capillaries (1). Finally, a physiological concentration (20 $\mu$M) of zinc was included in the assay as certain divalent cations have been reported to modulate angiogenesis (1). This experiment demonstrates that zinc, at a physiological concentration, has no effect on the angiogenic response.

The present invention may be used to determine which substances, in particular growth factors, are eliciting an angiogenic effect.

The growth factors acidic fibroblast growth factor (aFGF) and basic fibroblast growth factor (bFGF) are among the most potent angiogenic factors known (1). More recently vascular, endothelial growth factor (VEGF) has been identified as an important angiogenic factor, particularly in embryogenesis and solid tumours (1). Thus, the present invention was used to determine which growth factors were inducing the spontaneous angiogenesis observed in the in vitro assay (FIG. 4). It was found that, compared with control antibodies, polyclonal neutralising antibodies against bFGF and aFGF partially inhibited angiogenesis, with the anti-bFGF antibody being the more inhibitory. A mixture of the anti-bFGF and anti-aFGF antibodies was an even more effective inhibitor. In contrast, neutralising antibodies against VEGF had no effect on the angiogenic response. These data indicate that bFGF and aFGF, but not VEGF, play an important role in the in vitro angiogenesis assay described.

EXAMPLE 3

Screening of Substances for Angiogenesis Enhancement

A. Materials and Methods

Similar to Example 1 except that cultures were serum starved in order to reduce spontaneous angiogenesis. This step involved maintaining cultures in medium containing 20% foetal calf serum for the first 24 hours and then culturing the samples in serum free medium for the next 13–20 days with medium being changed every 3–4 days. Separate aliquots of substances suspected of possessing angiogenesis enhancing activity are added to individual wells as described in Example 2.

B. Results

FIG. 5 demonstrates the ability of different concentrations of the angiogenic growth factors bFGF, aFGF and VEGF to enhance angiogenesis in serum starved cultures. It was found that all three growth factors could enhance the in vitro angiogenesis response with slightly different dose response curves, although all growth factors induced a maximal response at 0.5 ng/ml and the lowest response at 50 ng/ml. Although not evident in FIG. 5, at 50 ng/ml VEGF induced substantial "die-back" of vessels as revealed by morphological changes in endothelial cells.

Although the assay depicted in FIG. 5 was performed using "serum starved" culture conditions, media containing minimal serum constituents for endothelial cell survival could be used when testing for substances which enhance angiogenesis.

The above examples demonstrate that the present invention may be used to assay substances which are known to have angiogenesis modulating ability. In addition substances, the angiogenic modulating properties of which are unknown, may also be tested.

The actual structure or composition of the substance to be tested is unimportant. The substance may be a relatively small molecule such as low molecular weight heparin, or even a more simple non-proteinaceous molecule through to a complex molecule or mixture of molecules such as antibodies of polyclonal or monoclonal origin. It is also envisaged that plant extracts, crude or refined, plant alkaloids or substances from other organisms such as microorganisms and marine life may be tested in the methods of the present invention.

The mechanism through which the substance exerts its angiogenesis modulating effect is unimportant. The mechanism may be through a particular growth factor or may act by inhibiting or promoting migration of cells or inhibiting or promoting tube formation which are prerequisites for angiogenesis.

EXAMPLE 4

Determining Whether an Angiogenic Entity will be Responsive to Anti-angiogenic Therapy.

This Example is directed towards use of the present invention in determining the appropriate treatment for an angiogenic entity such as a metastatic or invasive tumour.

A tumour sample from the patient may be processed to produce a tumour extract by freeze thawing of the human tissue or tissue cultured by standard tissue culture techniques then an extract of the sample produced. The sample is then tested according to Example 2 to determine whether the extract is angiogenic. The extract may be then further treated to separate, at least partially its constituents by standard biochemical or immunological affinity procedures and further screened according to Example 2 to determine which substance or substances are angiogenic. Once this information is obtained the appropriate anti-angiogenic treatment regime may be selected.

In addition to providing a method for selecting an appropriate tumour treatment regime, tumours and other angiogenic entities may be used in accordance with the present invention to isolate previously unidentified angiogenic enhancing agents for use in certain therapies.

References

1. Folkman, J. and Brem, H. (1992) Angiogenesis and inflammation. In: "Inflammation. Basic Principles and Clinical Correlates". Eds Gallin, J. I., Goldstein, I. M. and Snyderman, R. S., Raven Press, New York.
2. Folkman, J. (1985) Tumour angiogenesis. *Adv. Cancer Res.* 43, 175.
3. Folkman, J. and Klagsbrun, M. (1987). Angiogenic factors. *Science* 235, 442.
4. Folkman, J. (1985). Towards an understanding of angiogenesis: Search and discovery. *Perspect. Biol. Med.* 29, 10.
5. Langer, R and Folkman, J. (1976). Polymers for the sustained release of proteins and other macromolecules. *Nature* 263. 797.
6. Montesano, R., Orci, L. and Vassalli, P. (1983). In vitro rapid organisation of endothelial cells into capillary-like networks is promoted by collagen matrices. *J. Cell Biol.* 97, 1648.
7. Madri, J. A. and Williams, S. K. (1983). Capillary endothelial cell cultures: phenotypic modulation by matrix components. *J. Cell Biol.* 97, 153.
8. Kubota, Y., Kleinnmann, H. K., Martin, G. R. and Lawley, T. (1988). Role of laminin and basement membrane in the morphological differentiation of human endothelial cells into capillary-like structures. *J. Cell Biol.* 107, 1589.
9. Leibovich, S. J., Polverini. S. J., Shepard, H. M., Wiseman, D. M., Shively, V. and Nuseir, N. (1987). Macrophage-induced angiogenesis is mediated by tumor necrosis factor-alpha. *Science* 329, 640.
10. Montesano, R., Vassalli, J. D., Baird, A., Guillemin, R. and Orci, L. (1986). Basic fibroblast growth factor induces angiogenesis in vitro. *Proc. Natl. Acad. Sci.* 83, 7297.
11. Montesano, R., Pepper, M. S., Vassalli, J. D., and Orci, L. (1987). Phorbol ester induces cultured endothelial cells to invade a fibrin matrix in presence of fibrinolytic inhibitors. *J. Cell. Physiol.* 132, 509.
12. Nicosia, R. F. and Ottinetti, A. (1990). Growth of microvessels in serum-free matrix culture of rat aorta. A quantitative assay of angiogenesis in vitro. *Lab Invest.* 63, 115.
13. Knox, P., Crooks. S. Scaife. M. C. and Patel, S. (1987). Role of plasminogen, plasmin and plasminogen activators in the migration of fibroblasts into plasma clots. *J. Cell. Phvsiol.* 132, 501.
14. La Rocca, R. V., Stein, C. A., Danesi, R., Jamis-Dow, C. A., Weiss, G. H. and Myer, C. E. (1990). Suramin in adrenal cancer: modulation of steroid hormone production, cytotoxicity in vitro, and clinical antitumour effect. *J. Clin. Endocrinol. Metab.* 71, 497.

We claim:

1. A method for determining angiogenesis comprising culturing a blood vessel fragment derived from placental tissue together with a medium including a fibrin gel and suitable nutrients for a time sufficient and under conditions sufficient to allow growth of new vascular tissue, wherein the fragment is cultured in a culture volume of 1 ml or less and wherein said nutrients are replaced infrequently, and examining said fragment to determine whether new vascular tissue has grown.

2. The method of claim 1 wherein said fragment is of human origin.

3. The method of claim 1 wherein additional angiogenic agents are not added to the medium.

4. The method of claim 1 wherein the medium containing the suitable nutrients is 0.5 to 1 mL in volume.

5. The method of claim 1 wherein nutrient replacement is carried out less frequently than every second day.

6. The method of claim 1 wherein the fragment is 1 to 2 mm in diameter and less than 5 cm in length.

7. The method of claim 2 wherein additional angiogenic agents are not added to the medium.

8. The method of claim 1 wherein the medium containing the suitable nutrients is 0.5 to 1 mL in volume.

9. The method of claim 2 wherein the medium containing the suitable nutrients is 0.5 to 1 mL in volume.

10. The method of claim 3 wherein the medium containing the suitable nutrients is 0.5 to 1 mL in volume.

11. The method of claim 1 wherein nutrient replacement is carried out less frequently than every second day.

12. The method of claim 2 wherein nutrient replacement is carried out less frequently than every second day.

13. The method of claim 3 wherein nutrient replacement is carried out less frequently than every second day.

14. The method of claim 4 wherein nutrient replacement is carried out less frequently than every second day.

15. The method of claim 1 wherein the fragment is 1 to 2 mm in diameter and less than 5 cm in length.

16. The method of claim 2 wherein the fragment is 1 to 2 mm in diameter and less than 5 cm in length.

17. The method of claim 3 wherein the fragment is 1 to 2 mm in diameter and less than 5 cm in length.

18. The method of claim 4 wherein the fragment is 1 to 2 mm in diameter and less than 5 cm in length.

19. The method of claim 5 wherein the fragment is 1 to 2 mm in diameter and less than 5 cm in length.

20. The method of claim 1 wherein the fragment is 1 to 2 mm in length.

21. A method for testing substances for angiogenesis modulation activity comprising culturing a blood vessel fragment derived from placental tissue together with a medium including a fibrin gel, suitable nutrients and at least one substance suspected of having angiogenesis modulation activity for a time and under conditions sufficient to allow growth of new vascular tissue, wherein the fragment is cultured in a volume of 1 ml or less and wherein said nutrients are replaced infrequently, and examining said fragment for new vascular tissue growth and comparing said growth to that of a control.

22. The method of claim 21 wherein said angiogenesis modulation activity is inhibition of angiogenesis.

23. The method of claim 21 wherein said angiogenesis modulation activity is enhancement or promotion of angiogenic activity.

24. The method of claim 9 wherein said culture conditions comprise volumes of approximately 0.5 to 1.0 mL.

25. The method of claim 21 wherein said examination of the fragment is achieved by automated means.

26. The method of claim 21 wherein said substance is derived from material selected from the group consisting of a plant, an animal and a microorganism.

27. The method of claim 21 wherein a plurality of substances are cultured with a plurality of fragments separately.

28. The method of claim 21 wherein said fragment is approximately 1 to 2 mm in diameter and less than 5 cm in length.

29. The method of claim 21 wherein said biological sample is of human origin.

30. The method of claim 21 wherein said conditions provided include a substantially serum free medium.

31. The method of claim 21 wherein said examination of the fragment is achieved by computer analysis of an image of the fragment.

32. The method of claim 22 wherein a plurality of substances are cultured with a plurality of fragments separately.

33. The method of claim 23 wherein a plurality of substances are cultured with a plurality of fragments separately.

34. The method of claim 21 wherein said fragment is approximately 1 to 2 mm in diameter and 1 to 2 mm in length.

35. The method of claim 36 wherein said fragment is 1–2 mm in diameter and 1–2 mm in length.

36. A method for determining the ability of a substance to induce regression of new vascular tissue comprising culturing a blood vessel fragment derived from placental tissue together with a medium including a fibrin gel and suitable nutrients for a time and under conditions sufficient to allow growth of new vascular tissue, wherein the fragment is cultured in a culture volume of 1 ml or less and wherein said nutrients are replaced infrequently, administering the substance to said fragment, and culturing said fragment together with suitable nutrients for a time under the same conditions, then examining said fragment to determine whether regression of new vascular tissue has occurred.

37. The method of claim 36 wherein said fragment is of human origin.

38. The method of claim 36 wherein said fragment is 1–2 mm in diameter and less than 5 cm in length.

39. The method of claim 36 wherein said examination of the fragment is achieved by automated means.

40. A kit comprising in compartmentalized form at least one first compartment adapted to receive a fibrin gel for culturing of a blood vessel fragment in a culture volume of 1 ml or less, and at least one second compartment adapted to contain a nutrient medium for addition to the fibrin gel to support growth of a blood vessel fragment.

41. The kit of claim 40 wherein said at least one first compartment is adapted to receive 0.5 to 1.0 mL of medium.

42. The kit of claim 40 when used in the method of claim 9.

43. A method for determining the ability of a substance to induce regression of new vascular tissue comprising culturing a blood vessel fragment of human origin together with a medium including a fibrin gel and suitable nutrients for a time and under conditions sufficient to allow growth of new vascular tissue, wherein the fragment is cultured in a culture volume of 1 ml or less and wherein said nutrients are replaced infrequently, administering the substance to said fragment, and culturing said fragment together with suitable nutrients for a time under the same conditions, then examining said fragment to determine whether regression of new vascular tissue has occurred, and wherein said examination of the fragment is achieved by computer analysis of an image of the fragment.

44. The kit of claim 40 when used in a method for determnining the ability of a substance to induce regression of new vascular tissue comprising culturing a blood vessel fragment together with a medium including a fibrin gel and suitable nutrients for a time and under conditions sufficient to allow growth of new vascular tissue, wherein the fragment is cultured in a culture volume of 1 ml or less and wherein said nutrients are replaced infrequently, administering the substance to said fragment, and culturing said fragment together with suitable nutrients for a time under the same conditions, then examining said fragment to determine whether regression of new vascular tissue has occurred.

45. The kit of claim 40 when used in a method of determining whether an angiogenic entity will be responsive to anti-angiogenic therapy, the method comprising: culturing blood vessel fragments from said entity together with a medium including a fibrin gel, suitable nutrients and an effective amount of at least one anti-angiogenic agent for a time and under conditions sufficient to allow growth of new vascular tissue wherein the fragment is cultured in a culture volume of 1 ml or less and wherein said nutrients are replaced infrequently; examining said fragments for new vascular tissue growth; and comparing said growth to that of a control.

* * * * *

UNITED STATES PATENT AND TRADEMARK OFFICE
CERTIFICATE OF CORRECTION

PATENT NO. : 5,976,782 Page 1 of 1
DATED : November 2, 1999
INVENTOR(S) : Christopher Richard Parish, Kathryn Joanna Isabel Brown, Susan Faye Maynes, Anna Bezos It is certified that error appears in the above-identified patent and that said Letters Patent is hereby corrected as shown below:

<u>Column 13,</u>
Line 25, claim 24, change "9", to read --21--.

<u>Column 14,</u>
Line 21, claim 42, change "9", to read --21--.

Signed and Sealed this

Nineteenth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 5,976,782
DATED : November 2, 1999
INVENTOR(S) : Christopher Richard Parish et al.

It is certified that error appears in the above-identified patent and that said Letters Patent is hereby corrected as shown below:

<u>Title page,</u>
Item [73], Assignee, change "The Australian University, Australia", to read
-- The Australian National University, Australia --.

Signed and Sealed this

Twenty-sixth Day of August, 2003

JAMES E. ROGAN
*Director of the United States Patent and Trademark Office*